(12) United States Patent
Nagashima (10) Patent No.: US 6,907,350 B2
(45) Date of Patent: Jun. 14, 2005

(54) METHOD, SYSTEM AND APPARATUS FOR HANDLING INFORMATION ON CHEMICAL SUBSTANCES (75) Inventor: Renpei Nagashima, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 646 days.

(21) Appl. No.: 09/804,078

(22) Filed: Mar. 13, 2001

(65) Prior Publication Data

US 2002/0049771 A1 Apr. 25, 2002

Related U.S. Application Data

(60) Provisional application No. 60/188,682, filed on Mar. 13, 2000.

(51) Int. Cl.[7] .............................................. G01N 31/00
(52) U.S. Cl. ........................ 702/22; 702/19; 707/104.1
(58) Field of Search ................... 702/19, 22; 707/104.1

(56) References Cited

U.S. PATENT DOCUMENTS

| | | | | |
|---|---|---|---|---|
| 4,811,217 A | * | 3/1989 | Tokizane et al. ................ | 707/3 |
| 5,025,388 A | * | 6/1991 | Cramer et al. ................ | 700/293 |
| 5,418,944 A | * | 5/1995 | DiPace et al. .................. | 707/3 |
| 5,577,239 A | * | 11/1996 | Moore et al. ................... | 707/3 |
| 5,970,500 A | * | 10/1999 | Sabatini et al. .......... | 707/104.1 |
| 6,125,383 A | * | 9/2000 | Glynias et al. ............. | 709/202 |
| 6,185,506 B1 | * | 2/2001 | Cramer et al. ................. | 702/19 |
| 6,240,374 B1 | * | 5/2001 | Cramer et al. ................. | 703/11 |
| 6,421,612 B1 | * | 7/2002 | Agrafiotis et al. ............ | 702/19 |
| 6,434,490 B1 | * | 8/2002 | Agrafiotis et al. ............ | 702/27 |

FOREIGN PATENT DOCUMENTS

| | | | | |
|---|---|---|---|---|
| WO | WO 9727559 A1 | * | 7/1997 | ........... G06F/19/00 |

OTHER PUBLICATIONS

An et al., "3DinSight: An Integrated Database and Search Tool for Structure, Function and Property of Biomolecules" Trends in Glycoscience and Glycotechnology, Nov. 1999, vol. 11, No. 62, pp. 429–437.

David E. Clark et al.: Research Focus Reviews, Computational Methods for the Prediction of "Drug–Likeness';" DDT, Feb. 2000, pp. 49—58, vol. 5, No. 2, Elsevier Science Ltd.

Barbara A. Foster et al.: Science, "Pharmacological Rescue of Mutant p53Conformation and Function," Science, Dec. 24, 1999, pp. 2507–2510, vol. 286, American Association for the Advancement of Science.

Christopher A. Lipinski et al.: Advanced Drug Delivery Reviews, "Experimental and Computational Approaches to Estimate Solubility and Permeability in Dug Discovery and Development Settings," Advanced Drug Delivery Reviews, 1997 pp. 3–25, vol. 23, Elsevier Science B.V.

* cited by examiner

Primary Examiner—John Barlow
Assistant Examiner—Anthony T. Dougherty
(74) Attorney, Agent, or Firm—Foley & Lardner LLP (57) ABSTRACT

This invention provides libraries of information on chemical substances (which are termed "chenes") as they interact with various biological systems, efficient methods to construct such libraries, and data sharing systems which enable efficient utilization of such libraries. Furthermore, this invention provides data bases which accommodate and maintain libraries of information relative to such chenes, methods and systems to construct such data bases by accumulating those pieces of information which concern chenes as they interact with various biological systems, methods and systems to enable a client to search through such construed data bases for desired information, methods and systems to transmit to such a client such desired pieces of information concerning chenes that are housed in such data bases, tangible electronic means to record and make use of such systems and data bases, and apparatus to enable construction and search of such data bases and/or transmission of desired information to such a client.

22 Claims, 1 Drawing Sheet

Fundamental structure of data sharing system

Figure 1. Various concepts in chenomics

Figure 2. Fundamental structure of data sharing system

METHOD, SYSTEM AND APPARATUS FOR HANDLING INFORMATION ON CHEMICAL SUBSTANCES

This application claims benefit of Previsional application No. 60/188,682 filed Mar. 13, 2000.

FIELD

This invention relates to libraries of information on chemical substances (which are termed "chenes") as they interact with various biological systems, efficient methods to construct such libraries, and data sharing systems which enable efficient utilization of such libraries. Furthermore, this invention includes databases which accommodate and maintain libraries of information relative to such chenes, methods and systems to construct such data bases by accumulating those pieces of information which concern chenes as they interact with various biological systems, methods and systems to enable a client to search through such constructed databases for desired information, methods and systems to transmit to such a client such desired pieces of information concerning chenes that are housed in such data bases, tangible electronic means to record and make use of such systems and data bases, and apparatus to enable construction and search of such data bases and/or transmission of desired information to such a client.

BACKGROUND

Research for discovery and development of new drugs begins with exploration, identification, characterization, and validation of drug targets. Such drug targets are frequently selected from specific cell surface receptors, adhesion molecules, enzymes, substances that participate in intracellular transmission of information as is often called signal transduction, intra-nuclear receptors, transcription factors, cytokines, chemokines, inter-cellular substances, etc. Sometimes, specific tissues, organs, and whole animals (that are called experimental disease models when appropriate) as such are chosen as direct drug targets. Thereafter, screening methods are devised for such selected drug targets (wherein applied recently are automation, robotics, high-throughput settings, miniaturization, nanometrics, microfluidics, etc.), chemical libraries of various sources are screened for selected biological activity or non-activity by use of such screening methods (wherein technology of combinatorial chemistry is utilized to construct such chemical libraries when appropriate), so-called "hits" are identified, so-called "lead compounds" are generated by applying various algorithms to such hits, lead compounds are optimized to yield a single or multiple candidate compound(s) by considering so-called "drug-likeness" (for example, as described in Clark, D. E. and Picket, S. D., Drug Discovery Today (2000) 5: 49–58) and biological properties are observed in experimental animal systems. Thereafter, a candidate compound or compounds are formulated in the form of an appropriate preparation (now called a "drug product") and tested for safety and efficacy in humans, the size of target market and competitive advantage as well as disadvantage of a candidate drug product or products are studied, and, when all existent and foreseeable hurdles are recognized to be overcome by a drug product, an application is filed with a drug regulatory agency in a respective country or region (such as EC) for market release approval of the drug product.

Only after a compound in the form of drug product is approved by a drug regulatory agency of the respective country or region is it placed on sale in the market as a remedy for cure, treatment, or prophylaxis of a particular disease and associated symptoms. (While the term "compound" is used here, this term covers a wide range of substances and includes such biotechnology substances as proteins, enzymes, antibodies, etc. as are not obtained by chemical synthesis, and natural products such as natural antibiotics.) As understood from this description of drug research and development, there exists an enormous number of hurdles for a drug product to clear until it reaches a particular market.

Statistics of seventeen representative Japanese pharmaceutical companies during the period from 1992 to 1996 teach us that the success rate in drug development was one success that reached the market out of 6053 compounds that were synthesized (or obtained) and tested (DATA BOOK, 1999, Japan Pharmaceutical Manufacturers Association). Pharmaceutical industries in the United States of America and European countries also face similar difficulty and hardship in drug research and development. Accordingly, while an enormous number of compounds are synthesized (or prepared by other means) and tested, most of those compounds are dropped during research and development processes. In this specification, these compounds are termed "unsuccessful compounds."

A significant factor contributing to this low success rate is the difficulty in obtaining an appropriate list of "hit" compounds that would reasonably enable generation of lead compounds. Even if this difficulty is overcome, there is scarce chance of encountering good lead compounds. This would be so even if a validated drug target is identified and the most advanced technologies currently available for drug research such as high throughput screening, structure (/substrate)-based drug design (SBDD) and combinatorial chemistry are employed. While this is due partly to a limitation in the number and diversity of chenes that are proprietary and/or available to a company, a much greater problem arises from the fact that the lack of, or the poorness of, the science which serves to generate lead compounds from a given list of hits and optimize lead compounds to yield a desired drug product. In fact there is a widely recognized tendency where, since the introduction of HTS in drug research, those compounds synthesized in pharmaceutical houses have become greater in size with a significant fraction of compounds exceeding 500 in molecular weight and have demonstrated a tremendous increase in lipophilicity (as determined usually by octanol/water partition coefficient) and an associated decrease in solubility in water even to insolubility, and, as a result, lead compounds are as such difficult to be absorbed from the digestive tract (Lipinsky, C. A., et al., Advanced Drug Delivery Reviews (1997) 23: 3–25) and give little clues to improve and optimize them with respect to "drug-likeness" and other biological characteristics. Furthermore, for example, while many kinds of kinases are known to work in intracellular signal transduction pathways, science is lacking that teaches how to distinguish one kinase working in a specific manner from others that work in different manner and, more importantly, how to interfere with its action with a "drug-like" chene specifically. As a result, pharmaceutical houses are currently forced to repeat so-called random screenings with little confidence or assurance for success in finding a set of good hits or leads. Still another example concerns chenes which modulate protein-protein interactions. Certain people have come to share the view that these chenes need to be much larger in size than those which modulate small molecule ligand-protein interactions. While these large molecule chenes are suitable to interfere with the target protein-protein interactions, they are unable even to pass the cell membrane and reach inside the cell where such interference is needed. Protein-protein interactions are seen frequently in intracellular signal transduction and among transcription factors, and it is known that many pharmaceutical companies have selected these as drug targets. Unless science concerning chene-biological molecule interactions is discovered and advanced, and as long as some ways and means in drug designing methodology are discovered based upon science of such scope, it would be futile to discover a drug that would modulate protein-protein interactions and, accordingly for example, that would interfere with signal transduction pathways and interactions among transcription factors.

Recently, a group of relatively small molecule chenes have been discovered which, by acting in an allosteric manner after attachment, normalize the function of a mutant p53 protein which lacks the ability of the normal p53 protein to bind a specific DNA sequence (Foster, B. A. et al., *Science* (1999) 286: 2507–2510). This is an example of chenes which interfere with nucleic acid-protein interaction, which may share some degree of similarity to protein-protein interactions in the sense that interacting molecules are large in both cases. This discovery was, however, made as a result of random screening of as many as 100,000 compounds, so the success rate is still quite low.

There is also lack of science which serves to identify an appropriate drug target. As already mentioned, identification of a drug target is the first step in drug research and development. The lack of science in this respect is due largely to the lack of and, if it even exists, the poorness of, the science concerning interactions between chenes and the biological systems. Until chenes can be selected or created based upon the properties known to be possessed by desirable drug compounds, it is impossible to reasonably define the characteristics of a corresponding drug target and retrospectively, based on such characteristics, to construct a legitimate methodology to discover an appropriate drug target.

One of the most important reasons for seeing so many unsuccessful products is the lack of disclosure of data arising from in-house processes of research and development relative to drug products. While information and data concerning successful products and related compounds are frequently disclosed, those concerning unsuccessful compounds are accumulated only within respective houses and are totally unavailable even if people in academia and other pharmaceutical houses want to have access to those data.

Many pharmaceutical companies recently purchased commercially available chemical libraries and use them in screening for biological activities to obtain various data on chenes contained in such libraries. Data, however, are not disclosed and are destined to remain buried within those companies except for findings on certain chenes which have led to successful products. It often happens that different pharmaceutical companies screen chenes of the same commercially available libraries for the same biological activity and share the same failure and error in expectation for success. This constitutes duplication of developmental efforts and costs, and imposes burdens of waste on pharmaceutical companies. Such waste is found not only in pharmaceutical industries but also in other kinds of industries.

It is emphasized here that science is founded and advanced as a result of accumulation of information and data, i.e., facts. Without observations and facts obtained by such observations, any science cannot be founded and advanced. The lack of disclosure of information and data on most of the chenes studied in industries, except for those related to successful products, causes serious limitation to construction and advancement of science concerning chene-biological system interactions. The lack of opportunities for sharing information and data causes not only duplicative waste of efforts and costs in industrial research and development as mentioned in the preceding paragraph, but much more gravely hinders the development of an important branch of science. Science has its highest value in predictive power based on an established scientific rule or rules. Waste of efforts and costs is avoided if a rule or rules are discovered and proven by scientific studies. Science, for example, can give suggestions to what target will be appropriate (conversely, what target is inappropriate), what kind of chenes are desirable for a selected target and how one can find such desirable chenes. This kind of principles apply widely to chene-related industries.

DETAILED DESCRIPTION

An objective of this invention is to systematically relate a particular chene to its structural/physical chemical profiles and/or its functional profiles. By achieving this objective, this invention provides useful information for desired chemical substances (chenes) which display a profile of desired mode of interactions with the targeted biological system.

This invention further provides data sharing systems as a desirable means of effectively constructing information libraries on such chenes and efficiently utilizing such libraries. This invention, by providing such data sharing systems, enables collection of information rich in quantity and variety, accelerates the advancement of related science and technology and teaches how to avoid duplicative research and duplicative investments. As a result, this invention promotes rapid progress of research and development in industries.

In summary, this invention includes libraries of information on chemical substances ("chenes") as they interact with various biological systems, efficient methods to construct such libraries, and data sharing systems which enable efficient utilization of such libraries. Furthermore, this invention includes databases which accommodate and maintain libraries of information relative to such chenes, methods and systems to construct such data bases by accumulating those pieces of information which concern chenes as they interact with various biological systems, methods and systems to enable a client to search through such constructed data bases for desired information, methods and systems to transmit to such a client such desired pieces of information concerning chenes that are housed in such data bases, tangible electronic means to record and make use of such systems and data bases, and apparatus to enable construction and search of such data bases and/or transmission of desired information to such a client.

(1) Information Library of Chenes

The phrase "information library of chenes" of this invention is a library comprising certain chenes selected from chemical substances present in a given universe of chemical substances (chenome) that includes structural, physical, chemical, and/or functional data pertaining to such chenes.

The phrase "chenome" is used to refer to chemical substances in a manner analogous to the way that "genome" is used to refer to genes. Similarly, the phrase "chene" of this invention is analogous to "gene", and "chenomics" is analogous to "genomics".

Figure 1:
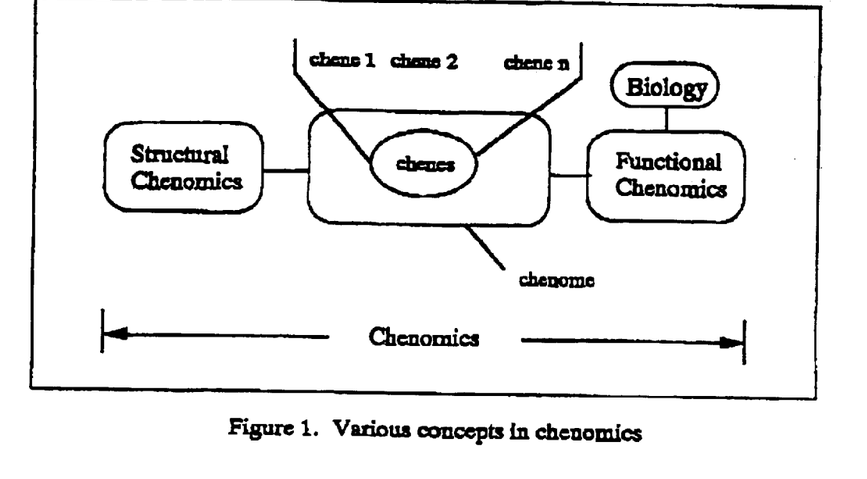
FIG. 1 illustrates various concepts in chenomics.

Genomics is a branch of science which studies the genome. When one refers to the human genome, it means both the sum of all genetic information possessed by the human cell and the whole of genetic materials carried by humans. While the genetic material is thought to be typically represented by DNA molecules, it should be remembered that RNA molecules are genetic materials in RNA-viruses and that prions are genetic materials in broad sense in prion disease. When one refers to about 3,000 mega base pairs of human genome, it means $10^9$ base pairs which form all of DNA molecules of the 22 pairs of autosomal chromosomes plus a pair of sex chromosomes. A gene is the most important element of the genome and is a specific sequence of DNA coding for a particular protein (polypeptide), and genetically the unit of transmission, recombination, and function (Ott, J., *Analysis of Human Genetic Linkage* (1999), 3rd Edition, p 3, The Johns Hopkins University Press). On the other hand, "chenomics" is a branch of science whose purpose is to study and clarify the relationship of all chemical substances (chenes) which can exist in this world with those substances which belong to the biological system as well as with the biological system itself. "Chenomics" includes structural chenomics and functional chenomics. In this specification, because the aspect of the interactions between chemical substances and the biological system is regarded as important, "structural chenomics" is defined as a sub-branch of chenomic science which concerns those chenes which have certain significance with respect to interactions with the biological system, or which can be present, with or without known significance, in the biological system. On the other hand, "functional chenomics" is defined as another sub-branch of chenomic science which studies the aspect of functions of the chene that are exerted on the biological system and, vice versa, functions of the biological system as exerted on the chene. FIG. 1 illustrates these concepts and emphasizes the relationship of chenomics with biology through functional chenomics.

Genomics, which studies the structure and the function of the genome, is an integration of structural genomics which concerns the structure of DNA molecules that carry the genome and functional genomics which concerns the function of each of the structural elements of the genome. As the determination of the genome sequence of various organisms, including that of humans, is ongoing, functional genomics is the field of study which is expected to grow rapidly. Such expectation for the rapid growth of functional genomics is based on the increasing trend of sharing the large masses of information among individuals and institutions. This has been made possible by the development of computational science and the global expansion of internet system. Science which deals with such information is called informatics and is being developed very rapidly. On the other hand, while communication science is connected with informatics in this area, it has yet to grow to the point of satisfying the current and future needs in informatics. The significance of this invention also lies here.

Information in genomics is not always shared publicly and openly. Such venture companies as Celera, Incyte, HGS and Gene Logic adopt a system of closed network with multiple private companies (sometime called "subscribers" who pay fees) and a limited number of academic collaborators.

This invention provides a system for sharing of "chenomic" information that is similar to the one developed in the field of genomics. ("chenomic" is the adjective, meaning "pertaining to chenomics.") However, it is not possible to construct an information sharing system in chenomics by simply imitating the genomic counterpart. Chenomics has unique situations of its own, different demands of its own to be satisfied, and problems peculiar to it to be solved. This invention has been made in consideration of these situations, for satisfaction of those demands, and by solving such problems. This invention is therefore expected to serve the future advancement of science and technology of chenomics-related fields in an effective and efficient manner.

The terminology "chenome" as used in this specification means the sum of all chemical substances that are and can be present in this world, and corresponds to the word "genome" as used in genomics. (The chenome includes naturally produced chemical substances as well as artificially produced chemical substances.) According to one theory, the number of different chemical molecules which are and can be present in this world, occupying the "chenome space" as termed here, is more than $10^{18}$ (Clark, D. E. and Picket, S. D. Drug Discovery Today (2000) 5: 49–58). This is to be compared with the $10^9$ base pairs of the human genome.

A "chene" as used in this specification means a chemical substance that is an important element of the chenome and corresponds to a gene, the most important element of the genome. A chene is a molecule and can be large (such as a polymer), small (like $H_2$ and glycerol) or intermediate in molecular weight. In principle, the concept of chene does not include, however, those molecules which form the environment (to be called "environmental molecule") such as molecular nitrogen and oxygen in the atmosphere and solvent molecules in a solution. It is to be noted that molecular oxygen or nitrogen present in water are regarded as a chene as it is not an environmental molecule under this circumstance. The definition of a chene thus depends on the situation.

There are a variety of parameters to describe the structural/physical chemical profile of a chene. Such profile is the subject of study in structural chenomics. The following are examples of parameters and expressions to describe such a profile. Structural formula by itself along with steric characteristics is one of the most important parameters. Molecular weight is a representative parameter which characterize the size of a chene. Polarity and dipole moment are examples of a parameter representing electromagnetic characteristics of a chene. The morphology of a chene can be expressed in a variety of ways, for example, linear (including string-like which implies flexibility), plane, disk-like, cubic, globular, conic, and various other expressions. Flexibility of the morphology also must be taken into consideration. Elongation and shrinkage, free movement, vibration and rotation are examples of such flexibility. Furthermore, when a chene is locally looked at, local morphology, electron density distribution, polar surface distribution, hydrogen bonding site distribution, hydrophobic surface distribution, van der Waals force distribution, etc. become important. Flexibility is to be considered also in these respects. In addition to expressions such as α-helix and β-sheet, to describe structural features, it is possible to employ such figurative expressions as chain, bridge, pocket, groove, door, broom, brush, key, key hole, wedge and the like. These figurative expressions are particularly useful for proteins, enzymes, peptides, nucleic acids, lipids and carbohydrates as the concept of a chene includes these molecules. The words like being buried, penetrate, perforate, and pierce may also used. Structural chenomics also deals with physical chemical characteristics which arise from interactions with non-biological systems such as solubility and stability in water or other aqueous and organic solvents. Structural features which influence these physical chemical characteristics are also dealt with by structural chenomics. The method of synthesis or preparation of a chene is desired to be included in structural chenomics data.

The functional profile of a chene is the subject of study in functional chenomics. The functional characteristics of a chene can have a variety of expressions, depending on the biological system in question (e.g., species of the organism, individual organism within that species, organ, tissue, cell, cell membrane, nuclear membrane, cytosol, intracellular organella such as nucleus, mitochondria, ER, Golgi apparatus, etc., cytosolic units such as ribosome, units composing each of the intracellular organella, and such biological molecules as proteins, enzymes, peptides, nucleic acids, lipids and carbohydrates). "Death" is one of those examples and can express the death of an individual organism (including man and animal), that of an organ, that of a tissue, and that of a cell (which is usually expressed by the term cytotoxicity), etc. Thus, a chene can cause death at various levels of the biological system. Particularly at the cellular level of death, the distinction between necrosis and apoptosis is well known. The same expression can have different meanings, depending on the level of the biological system in consideration; for example, degeneration can mean denaturation such as unfolding at molecular level for proteins and nucleic acids while the same terminology is used for description of pathologic changes of a cell or a tissue in similar (departure from nature) but different meanings such as fatty degeneration. Not only death and degeneration but other functional characteristics of a chene, regardless of whether it causes a positive (beneficial) or negative (harmful) change in the biological system, are described by morphological, biochemical and functional expressions. (In microbiology the term "phenomics" has recently been in use to describe morphological, biochemical and functional characteristics of a microorganism, which are classifiers in classic taxonomy, as opposed to "genomics" in modern taxonomy which utilizes the DNA sequence coding for ribosomal RNA among other classifiers.) Conversely, changes in a chene resulting from its interaction with the biological system are also included in the functional profile of a chene. Examples of such active (chene on biological system) and passive (biological system on chene) phenomena and properties include binding, association, coupling, affinity, adhesion, agglomeration, aggregation, grouping, repulsion, diffusion, dispersion, bridging, linking, transport, migration, movement, stimulation, activation, suppression, inhibition, avoidance, depolarization, excitation, emotion, affection, desire, volition, esterification, oxidation, reduction, alkylation, dealkylation, cell membrane permeability, bioavailability, degree of absorption of a chene via oral route, blood-brain barrier permeability, susceptibility to drug-metabolizing enzymes, elimination and excretion. (This is not meant to be an exhaustive list of examples.) The particular biological system where a change is caused by a chene, such as whole body, organ, tissue, cell, cellular organella, intracellular compositional unit or biological molecule, is to be included in the functional profile of a chene. Examples of passive change of a chene are hydrolysis by esterase when it is an ester and hydroxylation by drug-metabolizing enzyme when it contains an aromatic ring in its structure. Accordingly, the particular biological system which has caused a change in a chene, such as whole body, organ, tissue, cell, cellular organella, intracellular compositional unit or biological molecule, is to be included in the functional profile of a chene. Note here that a chene can not only be an exogenous molecule but also an endogenous molecule when it is viewed from the side of the biological system. When a chene is given in vitro or in vivo at a certain concentration or dose level, tissue or cell demonstrates a characteristic expression profile as indicated by quantitative changes in different mRNA species. This along with its time course is an important functional profile of a chene. Similarly, the proteomic expression profile as determined at the protein level (in lieu of the mRNA level) serves to characterize a chene in its functionality. The presence or absence of biological activity combined with the degree of that activity (if it is present) for a drug target as determined by appropriate assays is one of the most important data expressing the functional profile of a chene. This kind of activities are often expressed in terms of EC50, IC50, ED50, etc. Also, the data obtained from (human) clinical studies of a chene to see, for example, if there is an improvement in a particular disease or an associated symptom, constitute another important set of information characterizing the functional profile of that chene. Likewise, the functional profile of a chene as it relates to toxicity and safety is important. Examples of expressions for these aspects include cytotoxicity, animal toxicity (often expressed in terms of LD50 and pathologic changes whether macroscopic or microscopic), mutagenicity, teratogenicity, reproduction toxicity, clinical toxicity, clinical adverse reactions, etc. The functional profile of a chene can include data obtained on any species of organism, regardless of whether it is of animal (including man), plant or microbiological origin, and those obtained at any level of biological system, such as biological molecule, intracellular organ, cell, tissue, organ and individual (whole body). It is to be noted further that the functional profile of a chene does not preclude incorporation of data obtained in the presence of one or more different chene(s) in a specified biological system.

Such terminology as "cluster," "family," "species," "ortholog" and "homolog" as employed in this specification is similar in its meaning to that used in genomics and evolutionary genomics. In chenomics, however, these terms are used to express not only similarity and type/closeness of relationship (as used in phylogenic genomics) in the "structure" of two or more chenes, but also similarity and type/closeness of relationship in the "function" of two or more chenes. Distinction in terminology is achieved by naming one as "structural cluster" and the other as "functional cluster." An example of a structural cluster is a group of chenes which share the same scaffold when combinatorial chemistry technology is used in a synthetic work. On the other hand, an example of a functional cluster is a group of chenes which demonstrate identical, similar or closely related expression profiles (as determined by mRNA levels) in a specified cell (type) or tissue. It is suggested in this specification that variant, species, cluster, and family are used in an increasing order of population. Such terminology as "ortholog" and "homolog" are conveniently used in chenomics to express the relationship of two or more chenes as obtained by analysis of data according to certain rules that are similar to those used to delineate the phylogenic relationship in evolutionary genomics. For example, a group of chenes having the same functional group or groups but with slightly different scaffolds in their structures may be called orthologs. The use of these words in expressing phylogenic relationship of different functional profiles may become possible when interactive chains of events in the biological system at molecular level are clarified.

Such words as "pathway," "cascade," "network," and "crosstalk" are used in this specification to mean the same concepts as used commonly in molecular biology although "network" and "networking" are used elsewhere also for data transmission.

The "information library of chenes" in this invention is particularly useful for identifying candidate compounds (chenes) with desired effects in the process of drug discovery and development. For example, when one desires to select a compound or compounds with a specific action on the biological system and places a query in this library with a set of keywords which indicate that specific action, one can obtain a list of compounds having queried action with their structural and functional profiles. Examination of the output data will give a distinctive idea about what compounds exhibit the specified action and what other compounds do not. As both structural and functional data are obtained, an efficient process of drug discovery is made possible. Instead of specifying a single action, one can also place an appropriate query to obtain a list of chenes with desired sets of structural and functional profiles such as flavones with high affinity for IL-6 receptor, low cytotoxicity, an appropriate range of drug-likeness parameter values and certain indication for what drug-metabolizing enzyme system is involved. If it becomes known that there is no such chene in the library, one can relax the conditional requirements in query until one obtains a certain image about what structural requirements will have to be met for a desired chene.

As will be described subsequently, by incorporating appropriate software in the library, it would even become possible to "predict" what chene would most desirably meet queried requirements, what its structure is and how to synthesize it. This is a surprising advantage of the information library of chenes and this kind of use of the information library of chenes is expected to tremendously accelerate the discovery and development of useful drugs.

(2) Construction of Information Library of Chenes

The information library of chenes in this invention can be constructed on the basis of internal information belonging to a single individual, a single company, or a single organization or group. Also the information library of chenes in this invention can be constructed by integration of information from multiple sectors selected from individuals, companies, organizations and groups. Further, such information can be publicly known or unknown, i.e., novel.

Generally speaking, much of information on chemical substances is hidden within the framework of a private enterprise and rarely or only occasionally disclosed publicly. This can pose a formidable restriction on the advancement of science. Even if publicly disclosed, the chemical substance in question may be protected to a degree by intellectual property right or by filed patent application against its synthesis, preparation, access and use.

Particularly, as described previously, information and data relative to those chenes which have been prepared for the purpose of drug research and development are largely buried within the company that has studied them and are rare to be publicly disclosed unless a success is achieved. The opportunities thus are largely limited for different companies and academic researchers to be able to share such information and data. This is undesirable in view of foundation and advancement of related science.

It is therefore desirable to construct such systems as mentioned below by which concerned parties can share relevant information and data and effectively establish and advance related science, i.e., "chenomics, " as a result of researching on such information and data.

(3) Data Sharing Systems

It is necessary to caution here that science is not under monopoly of so-called academia. It is possible to construct and share science at the level of private industries only, if there is a legitimate reason for it. On the other hand, it is also possible to invite academic researchers for collaboration with private industries if certain conditions are met.

There are several reasons for the fact that each company has a tendency of hesitating to publicly disclose information and data obtained in-house. This invention includes practical means to reduce such tendency by eliminating the causes for such hesitation. With this invention it is likely that each company and its researchers become willing to submit their information and data, and will enjoy the opportunity of sharing a pool of data that have been collected, accumulated, integrated and disseminated. Also, academic researchers will be pleased to collaborate with the industrial sectors if imposed conditions are acceptable to them.

Furthermore, in this invention, it is possible to add sub-systems and systems parallel to the original ones. This invention includes each of these added systems and the whole after addition of one or more of selected parallel system(s) and/or sub-system(s). An example of such additional system is, as described in the preceding section, when a set of requirements are defined in a query, one which can predict what chene would most desirably meet queried requirements, what its structure is and how to synthesize it. This can be called "in silico drug design and synthesis by reverse screening." Such a system integrated as whole is expected by itself to automatically generate novel findings in chenomics as the amount of data and information is cumulatively increased with time. In other words, the system of this invention is a system which "does science" of its own and by itself.

Description has been made with pharmaceutical industry as an example that certain disturbing situations and problems in this industry can be solved by this invention. Such situations and problems, and corresponding solutions provided by this invention almost equally apply to other industries which are associated with use and production of the chene. Examples of such other industries include, but not limited to, chemical, food, agricultural, environmental, and health industries. In addition, this invention is expected to serve information industry and communication industry as it relates to information and communication.

The system of this invention with associated features has not been described nor has been in existence in the past and therefore is novel. The system of this invention with associated features has not been suggested nor proposed in the past and therefore is a truly epoch-making system.

The present invention is further illustrated by, though in no way limited to, the following examples.

EXAMPLES

Explanations are given in detail below with certain examples chiefly on data sharing systems of this invention. The scope of this invention, however, is not limited to by these examples.

Example 1

Fundamental Structure

Figure 2:
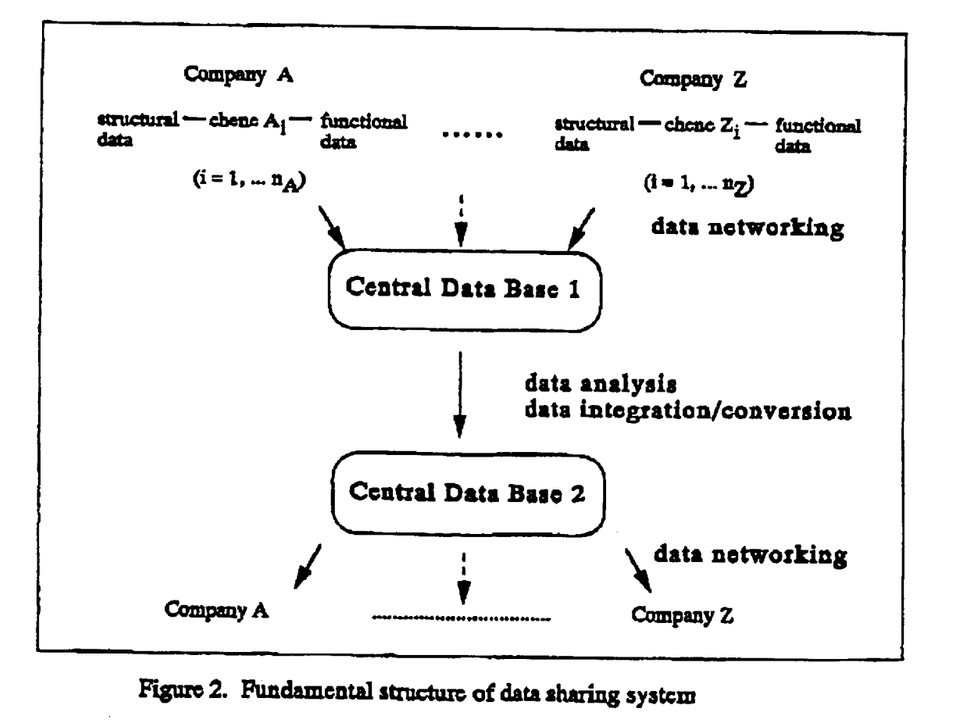
FIG. 2 illustrates the fundamental structure of a system according to the invention for sharing and interrelating information and data pertaining to chenomics.

The fundamental structure of this invention is shown in FIG. 2. There can be innumerable structures which are derived from the fundamental structure and by combination thereof. The upper part of FIG. 2 indicates both structural and functional data concerning a plurality of chenes which are possessed by each of different member companies. (The word "member" can be interchangeably used with client.) These data are first sent, for example by a closed means and/or systems of communication, to Central Data Base 1 (data networking) and accommodated and stored there. While the terminology of "member company" is used in FIG. 2, the membership is not limited to a company but is open to an individual or a group formed by specific individuals; for example, individuals belonging to a particular laboratory of a company or academia are also eligible. However, as described subsequently, member company, individual member, and each individual belonging to group must observe certain rules for confidentiality. Violation of these rules may be accompanied by a reasonable amount of punishment and cancellation of its, his or her membership. Each set of the data accommodated in Data Base 1 is examined upon receipt for its reliability automatically by a set of computer programs and/or semi-manually (a set of data with dubious reliability is returned to the originator with appropriate comments), those sets of data passing the receipt examination are analyzed and classified (data analysis) and integrated (data integration) in the pool of already collected data. The process of data analysis utilizes a set of computer programs and systems and includes conversion of data which enables both retrieval of requested data in response to a query by a member and transmission of the requested data to the member. The collected data are converted in this manner, integrated in the pool of already collected data and accommodated and stored in Central Data Base 2. When a query is received from a member, relevant data are retrieved from the integrated data base stored in Central Data Base 2 and sent to the member, for example, by a closed means and/or closed systems of communication (data networking). With accumulation of data and information with time, this system becomes increasingly valuable for members who share such data and information. Unless returned on receipt of data for reason of dubious reliability, data once stored in Central Data Bases 1 and 2 should not be destroyed or discarded. As described subsequently, this is because there may arise a need in later times to determine who submitted a particular set of data first. It is desirable for the system to be equipped with a completely duplicative back-up system which is to be activated in case of an unforeseen accident. Similar precaution is to be applied to computer programs. This system is constructed in such a manner as to be inaccessible to outsiders and protected against any attempt to disturb its function by unauthorized personnel.

Example 2

Structures to Promote Submission and Sharing of Information; Sub-types of the System The system of this invention is basically closed, but it is possible to construct various sub-types of the system which are to various degrees open to different members. These sub-types are called "semi-closed" systems.

As companies are frequently competitive with each other, they usually pay their best attention to avoid leakage of information which results in certain advantage to their competitors. In other words, they do their best efforts to protect their confidential information from leakage. Accordingly, it is understandable that they more or less tend to hesitate to participate in this kind of system. Because disclosure of information is guaranteed to be limited to a defined group of members in a perfectly closed system, they would prefer it to semi-closed ones.

The smallest of this system in terms of the number of members is the one in which disclosure of information and sharing is limited within a company. In this case, a person who wants to practice this invention can construct a closed system according to this invention and sell it to multiple clients or sell customized versions to different clients.

It is possible for two or more companies to form a consortium. If they are not competitive in the market for reason of being in different industries, for example, they may even be willing to participate in such a consortium.

Even among competitive companies, it is possible to form a mini-consortium by limiting the extent of data sharing to a specific cluster or family as defined by either structural chenomics or functional chenomics, or both. The value of this invention lies also in this device to stratify areas of information to enable this kind of limited collaboration. This can be called stimulation of data sharing by "data stratification."

Again, a person who wants to practice this invention can construct a closed system that suits a group of different company members and sell it to such a consortium or mini-consortium.

In order to absolutely encourage data submission and promote data sharing, on the other hand, various systems are devised as follows.

One of the means is patent application. Once a patent application is filed on various attributes of a certain structural cluster or a functional cluster or both of chenes, the legal position of the applicant becomes guaranteed to a degree and, for that applicant, it would become easier to submit relevant data to data bases of this invention. It is recommended to a person who wants to practice this invention for sale to encourage patent application by members of consortium or mini-consortium.

Furthermore, particularly in a closed system, members (including academic members who guarantee defined confidentiality requirements for that closed system) can mutually agree on, for example, information receiver's guaranteeing to give certain right resulting from the use of information to the originator of the information who submitted it first, or pay a certain amount of money to such an originator. In this case, while a patent application may or may not have been filed on the subject, the amount of guaranteed return either in the form of right or money or both is influenced by the presence or absence of patent application and the contents and value of that patent application. Again, prior patent application is highly recommended to increase the value of information. It is further recommended for members to agree on a clause according to which, when members find a difference in dispute, they can bring the case to a neutral arbitration agency or organization for settlement. This would give a certain amount of easiness and encourage submission and sharing of their data. All these agreements are recommended to be in documentation and such documentation can be maintained in the system of this invention under strict confidentiality. These measures for agreement are included in the system and associated features of this invention.

A semi-closed system is formed by imposing different kinds and degrees of restriction on an open system. When such restriction reaches a maximum, the system practically returns to a closed system. An effective measure for such restriction is to "stratify" and/or "give certain hierarchy to" data and information accessible to members other than originators. By taking this measure, it becomes possible to allow for non-originator members to have limited access to information and data. The degree and extent of such access is determined on the basis of who wants such access and the amount of guaranteed return in right and/or money. As restriction is strengthened, submission of data and information by members will be accelerated. This and other collateral measures are incorporated in this invention.

Who wants to have access to data and information (data seeker) is a critical factor in granting such access. This can be determined on the basis of whether the data seeker belongs to industry or academia (also whether seeker-affiliated academic institution is public or private) and, if data seeker is a company, what industry it is in, number of employees, sales volume, total capital and other financial indicators, attained success in relevant area, strength of commitment in the field pertaining to the data and information, etc. In addition, it is desirable for the originator to have right and freedom to choose an eligible data seeker to be given such access without duty to disclose to any party the reason for the choice. Also data seeker can have confidential information of his or her own which benefits the originator directly or indirectly. In such a case, data seeker can add its value to guaranteed return for receiving information. This may require negotiation, the scheme of which as outlined here is incorporated in the form of networking sub-system in this invention.

Stratification of data and information has already been explained.

Hierarchy of data and information means hierarchy by which the level of disclosure by the originator can be determined. The level of disclosure by the originator can be determined by whether or not the originator is comfortable with that level of disclosure and further depends, for example, on who seeks access to relevant data and what degree and extent of return is guaranteed. This hierarchy is basically determined by the originator, who, for example, may have in advance classified potential data seekers, graded the value of guaranteed return and assigned an appropriate stepwise hierarchy to submitted data and information. This process may also require negotiation, the scheme of which as outlined here is incorporated in the form of networking sub-system in this invention.

When a data seeker desires to have access to certain integrated data originating from multiple parties, this is basically to be settled by negotiation with each of the originators. A sub-system can be incorporated to enable prior determination of the value of data at the time of data submission numerically according to a certain rule. Reference to this numerical value of that set of data may be able to resolve difficult disputes among multiple members. For example, a proportionate return as determined in reference to such numerical values is expected to settle potential disputes easily. Depreciation can occur in the predetermined value when, for example, corresponding patent application is later published and when there is a third party who has publicly disclosed the same information prior to publication of the patent application in question. The previously mentioned sub-system incorporates this aspect also.

The reverse auction system first invented for sale of airline tickets (U.S. Pat. No. 5,797,127), when adopted and incorporated, is an effective means to improve the value of the system of this invention. When incorporated in this invention, a data seeker presents to the system maximum guaranteed return in exchange for presentation to the system of requested data defined, for example, by structural and/or functional cluster, family, etc. The originator who has submitted the requested data is searched for and identified by the data seeker (closed system) or system administrator (closed or semi-closed system) or the originator himself or herself. The originator is advised of the data seeker and associated information on the data seeker through the system and make a bid for requested return. Who has bid the minimum return gives the data seeker right to look at and use requested data. Particularly, when such a situation is reached that duplicative data from different originators have been accommodated in the system, this method is expected to promote data submission and sharing.

Example 3

Integration of Data and Information

Data and information are preferably be in predetermined format but this is not necessarily an absolute requirement. Received data can be transformed into the predetermined format by the system with the use of appropriate software and/or semi-manually. The data thus transformed are analyzed, classified, and integrated for dissemination and search by members in the pool of previously accumulated data by the use of commercially available software as each company is doing in-house. For chenes, in terms particularly of structural chenomics, the methods of CAS can be followed. For both structural/physical chemical data and functional data, the methods of Derwent Information can be followed. Commercially available software such as ISIS Base, ISIS Draw and its improved versions (e.g., that of Molecular Design Ltd.) are useful for this purpose. The data thus integrated is housed and maintained in Data Base 2 as illustrated in FIG. 2.

The system can "do science" of its own and by itself. The system of this invention has a multitude of incorporated programs to be used for statistical analysis which summarize multivariate relational data and put them into integration which suits each of specific purposes. This is equivalent to scientific research. For example, the system can stratify the data on chenes into appropriate clusters or families, can assign certain phylogenic or hierarchial positions to chenes such as ortholog and homolog according to their structural/physical chemical profiles and functional profiles, and can structure the data in the form of pathway, cascade, network and crosstalking relationship. This can be done on both structural/physical chemical data and functional data, separately, and the results obtained are useful in advancement of science and technology. However, when a correlation is found between certain sets of structural and functional data and further when certain rules are discovered and validated between structure and function, the value of such analyses incorporated in the system attains its maximum. "In sillico drug design by reverse screening" previously referred to comes readily to reality when such maximum is reached.

Examples of the methods for statistical analysis to be incorporated in the system include, generally speaking, multivariate regression analysis, principal component analysis and its variants, canonical correlation analysis, multivariate analysis of variance, discriminant function, and cluster analysis. Corresponding software is available for free or commercially. The Markov Model Method and its variant, the Hidden Markov Method, have yielded interesting conclusions in the field of genomics in terms of phylogenic analysis and study of similarity between different genes within the same species of organism or traversing different species. These latter methods are expected to be particularly useful for the system to "do science."

Example 4

Connection with Public or Non-public Data Bases and Co-integration

Public data bases can be connected with and integrated in the system of this invention. In chemistry, there is CAS-ON-LINE. Examples of genomic and proteomic data bases include NCBI, EBI, EMBL, and DDBJ.

Connection with non-public data bases and integration is desirable if terms and conditions are acceptable. Examples include WDI (Derwent Information), Comprehensive Medical Chemistry (CMC, MDL Information Systems) and Available Chemicals Directory (ACD, MDL Information Systems).

Utility and Possibility for Industrial Application

This invention serves to study the relationship between all the chemical substances that are and can be present in this world, regardless of whether known or unknown, and the biological system and substances belonging to the biological system, and contribute to the advancement of related science and industrial technology. The fields of science which are given contributions by this invention include medical science, pharmacology, pharmaceutical science, medicinal chemistry, toxicology, environmental science, agricultural science and engineering. Industries which benefit from this invention include pharmaceutical industry, health industry, chemical industry, food industry, agrochemical industry, plant industry, environmental industry, information industry and communication industry.

It will be apparent to those skilled in the art that various modifications and variations can be made to the method, system and apparatus of this invention. Thus, it is intended that the present invention cover such modifications and variations, provided they come within the scope of the description and their equivalents.

The disclosure of all publications cited above are expressly incorporated herein by reference in their entireties to the same extent as if each were incorporated by reference individually.

I claim:

1. A method for handling information in which a set of structural data and functional data of a chemical substance, which is internal information of a single individual or a single company or a single organization or a single group, is related and accommodated in a data base and such related set of data is analyzed and classified, and further converted in a form which enables corresponding individual or company or organization or group who has submitted the original set of structural data and functional data to conveniently search for needed information at later times, and accommodated and cumulatively stored in another data base.

2. A data base constructed by the method according to claim 1.

3. A method according to claim 1 to relate a set of structural data and functional data of a plurality of chemical substances.

4. A method according to claim 1 to analyze and classify, and further convert a set of structural data and functional data of a plurality of chemical substances in a form which enables individual or company or organization or group who has submitted the original set of structural data and functional data to conveniently search for needed information at later times, and accommodate and cumulatively store such converted data in a data base.

5. An information library of chemical substances constructed according to the method in claim 1.

6. A system comprising the information library constructed according to claim 5 and means to enable individual or company or organization or group who has submitted the original set of structural data and functional data to search for needed information at different times.

7. A method for handling information in which a set of structural data and functional data of each of chemical substances possessed internally by multiple sectors selected from individuals, companies, organizations and groups of individuals is related and accommodated in a data base and such related set of data is analyzed and classified, and further converted in a form which enables a person to conveniently search for needed information at later times, and accommodated and cumulatively stored in another data base.

8. A database constructed by the method according to claim 7.

9. A method according to claim 7 to relate a set of structural data and functional data of a plurality of chemical substances.

10. A method according to claim 7 to analyze and classify, and further convert a set of structural data and functional data of a plurality of chemical substances in a form which enables a person to conveniently search for needed information at later times, and accommodate and cumulatively store such converted data in a data base.

11. An information library of chemical substances constructed according to the method in claim 7.

12. A system comprising the information library constructed according to claim 11 and means to enable a person to search for needed information at different times.

13. A method for handling information on chemical substances, comprising:
    identifying a set of structural data and functional data of a chemical substance internally by an entity;
    relating and accommodating the set of structural data and functional data of a chemical substance in a first data base;
    analyzing and classifying the related set of data;
    converting the related set of data in a form which enables the entity who has submitted the set of structural data and functional data to conveniently search for needed information at later times;
    accommodating and cumulatively storing the converted related set of data in a second data base; and
    accessing the second data base and searching the second data base for needed information, wherein the entity accessing the second data base is the same entity who has submitted the set of structural data and functional data.

14. A computer system for implementing the method of claim 13.

15. The method according to claim 13, wherein a set of structural data and functional data of a plurality of chemical substances is related.

16. An information library of chemical substances adapted to be used when practicing the method according to claim 13.

17. A system comprising the information library constructed according to claim 16, wherein the information library is adapted to enable the entity who has submitted the original set of structural data and functional data to search for needed information at different times.

18. A method for handling information on chemical substances, comprising:
    selecting a set of structural data and functional data of chemical substances possessed internally by a plurality of sectors;
    relating and accommodating the selected set of structural data and functional data in a first data base;

analyzing and classifying the data;

converting the data into a form which enables a person to conveniently search for needed information at later times;

accommodating and cumulatively storing the converted data in a second database; and accessing the second data base and searching the second data base for needed information, wherein the person accessing the second data base is associated with at least one of the plurality of sectors who had internally possessed the data.

19. A computer system for implementing the method of claim 18.

20. The method according to claim 18, wherein a set of structural data and functional data of a plurality of chemical substances is related.

21. An information library of chemical substances adapted to be used when practicing the method according to claim 18.

22. A system comprising the information library constructed according to claim 21, wherein the information library is adapted to enable a person associated with the at least one of the plurality of sectors to search for needed information at different times.

* * * * *